United States Patent [19]

Wideman et al.

[11] 4,131,629

[45] Dec. 26, 1978

[54] SELECTIVE HYDROGENATION OF CYCLOPENTADIENE TO CYCLOPENTENE USING RANEY NICKEL CATALYST AND WATER IN THE REACTION MIXTURE

[75] Inventors: Lawson G. Wideman, Akron; Ellert A. Ofstead, Cuyahoga Falls, both of Ohio

[73] Assignee: The Goodyear Tire & Rubber Company, Akron, Ohio

[21] Appl. No.: 850,580

[22] Filed: Nov. 11, 1977

[51] Int. Cl.² ............................................. C07C 5/02
[52] U.S. Cl. ................................. 260/666 A; 260/667
[58] Field of Search ........................... 260/666 A, 667

[56] References Cited

U.S. PATENT DOCUMENTS

| | | | |
|---|---|---|---|
| 2,360,555 | 10/1944 | Evans et al. | 260/666 A |
| 3,637,877 | 1/1972 | Nowack et al. | 260/666 A |

*Primary Examiner*—Veronica O'Keefe
*Attorney, Agent, or Firm*—J. Y. Clowney

[57] ABSTRACT

There is disclosed a process for the preparation of cyclopentene which comprises selectively hydrogenating cyclopentadiene in the liquid phase by contacting cyclopentadiene with hydrogen in the presence of a hydrogenation catalyst comprising a highly dispersed form of nickel in which water is employed in the reaction medium.

5 Claims, No Drawings

SELECTIVE HYDROGENATION OF CYCLOPENTADIENE TO CYCLOPENTENE USING RANEY NICKEL CATALYST AND WATER IN THE REACTION MIXTURE

BACKGROUND OF THE INVENTION

This invention is directed to a selective hydrogenation of dienes to monoolefins, particularly of cyclopentadiene to cyclopentene. More specifically, it is directed to a process whereby cyclopentadiene is selectively hydrogenated to cyclopentene with the use of a highly dispersed form of nickel as a catalyst and water as a reaction medium.

At the present time, substantial amounts of cyclopentadiene, usually as dicyclopentadiene, are available as a byproduct from the steam cracking of gas oil or naphtha, a process which produces primarily ethylene. Cyclopentene has been found to be useful as a monomer for the formation of general purpose elastomers by ring opening polymerization of cyclopentene. Therefore, it is desirable to convert a portion of the excess cyclopentadiene available into a more valuable raw material, such as cyclopentene.

The hydrogenation of cyclopentadiene to cyclopentene is not new. For instance, in U.S. Pat. No. 2,360,555, issued Oct. 17, 1944, there is disclosed a selective hydrogenation of one of the two conjugated double bonds of a cyclic diolefin to produce the corresponding cyclic monoolefin, which is accomplished by conducting the hydrogenation in the liquid phase in the presence of an active hydrogenation catalyst, under moderate hydrogen pressure, such as 2 to 5 atmospheres absolute, and at relatively low temperatures, such as from 0° to 40° C. and even up to 100° C., using substantially less than the stoichiometric amount of hydrogen theoretically required to completely reduce the cyclic diene to the corresponding cyclic monoolefin. The catalyst therein disclosed is a pyrophoric nickel metal catalyst, such as Raney nickel. It is also disclosed that it is desired to conduct the reaction in dilute solution. The dilution may be affected by the addition of any solvent, stable under conditions of the process and which is not a catalyst poison and whose boiling point is such as to render it easily separable from the reaction mixture. Benzene and ethanol as well as tetralin, dioxane, isooctane, ethyl ether and diisopropyl ether are disclosed as such solvents in such process.

In U.S. Pat. No. 3,819,734, issued July 25, 1974, there is disclosed the hydrogenation of cyclopentadiene to cyclopentene by bringing cyclopentadiene into contact with a catalyst consisting essentially of (1) nickel, on a magnesium or zinc oxalate support, (2) a ligand selected from the group consisting of trimethyl phosphine, triethyl phosphine, methyl ethyl propyl phosphine, trimethyl phosphite, triethyl phosphite, tributyl phosphite, triphenyl phosphite, etc., while in the presence of hydrogen, at temperatures from 0° C. and at pressures from 0 to 1000 pounds per square inch gauge. The solvent mentioned therein is ethanol.

In U.S. Pat. No. 3,994,986, issued Nov. 30, 1976, there is disclosed the preparation of cyclopentene from cyclopentadiene by hydrogenating cyclopentadiene with hydrogen gas at a ratio of 1 to 1.5 moles of hydrogen per mole of cyclopentadiene in the presence of a palladium catalyst on a carrier.

Also, in U.S. Pat. No. 3,857,894, issued Dec. 31, 1974, there is disclosed the hydrogenation of a cylopentadiene to cyclopentene in the presence of a palladium catalyst and a catalytic amount of an aqueous solution of a zinc salt having a water/zinc ratio of at least 1/1 by weight.

The cyclopentadiene employed in the formation of cyclopentene by hydrogenation is usually obtained by depolymerizing or cracking dicyclopentadiene. In order to obtain cyclopentadiene for the hydrogenation of this invention, the depolymerization of dicyclopentadiene is accomplished by heating the dimer at a temperature above 150° C. under atmospheric pressure in a conventional cracking apparatus. The depolymerized material should be hydrogenated without substantial delay because it is also known that redimerization will occur upon standing.

SUMMARY OF THE INVENTION

According to the invention, cyclopentadiene can be selectively hydrogenated to cyclopentene in the liquid phase by contacting cyclopentadiene with hydrogen in the presence of a catalyst comprising a highly dispersed form of nickel and in which water is employed as a reaction medium.

It has been found that in order to have a fairly selective hydrogenation for cyclopentene, a reaction medium or a diluent must be employed. According to the present invention, water is employed as a reaction medium.

Certain advantages are inherent in the use of water as a reactive medium. The presence of water aids greatly in moderating the exothermic nature of the hydrogenation of cyclopentadiene. The use of water provides an almost effortless method of removing the reaction medium from the mixture of unreacted cyclopentadiene and the product cyclopentene because these form a two-phase system. Cyclopentadiene and cyclopentene are not soluble in water. Thus, one phase consists of the hydrocarbon mixture of unhydrogenated cyclopentadiene and the hydrogenated product cyclopentene. Another advantage in using water as a reaction medium allows the cyclopentadiene feedstock which has been formed by the steam cracking of dicyclopentadiene to be employed in an undried form.

DETAILED DESCRIPTION OF THE INVENTION

The temperature at which cyclopentadiene may be hydrogenated in accordance with this invention may range from 0° to 75° C. with 20° to 30° C. being most preferred. Temperatures that approach 100° C. tend to consume the cyclopentadiene in side reactions, such as dimerizations back to dicyclopentadiene and other undesirable side reactions. Generally speaking, both the temperature and the pressure of hydrogen employed should be kept as low as possible consistent with reasonable rates of hydrogenation. When faster rates of reaction than that being obtained is desired, it is preferable to increase the rate of hydrogenation by means of increased hydrogen pressure rather than an increase in the temperature.

High hydrogen pressures may be employed to effect faster rates of hydrogenation, however, it has been found in accordance with the present invention that about 150 psig, about 1035.5 kPa, is all that is required to give a reasonable rate of reaction.

The reaction medium, which is water, is not conducive to the solubility of the cyclopentadiene and thereby renders the process a two-phase system that requires some vigorous agitation. Upon agitation, the water serves as a heat sink by absorbing unwanted heat from the reaction site and, hence, moderates the hydrogenation, thereby enhancing the selectivity for the desired product.

The presence of a two-phase system when the agitation is stopped also offers the advantage that the catalyst settles to the bottom of the lower aqueous layer and no residual hydrogenation of the organic layer occurs if a lengthy time is required to remove the reaction product, cyclopentene. Water also serves to protect the catalyst from air and thereby facilitates an easy recycling of the catalyst.

The catalyst employed in the present invention is a highly dispersed form of nickel. However, a Raney nickel-type catalyst is preferred. Methods for preparing the Raney nickel catalyst which are useful in this invention are known and can be found in a book entitled "CATALYTIC HYDROGENATION", by Robert L. Augstine, published in 1965 by Marcel Dekker, Inc., New York, N.Y.

Temperatures employed to prepare Raney nickel do not vary widely and are disclosed in this reference. The author refers to these Raney nickel catalysts as W1, W2, W3, W4, W5, W6, W7 and W8. In addition to the W-type Raney nickel, a Raney nickel referred to as T-1 is preferred, or a modification of T-1 Raney nickel is preferred.

In the Journal of Organic Chemistry 26, 1625 (1961), there is described a process for the preparation of what the authors refer to as T-1 Raney nickel by Dominguez, Lopez and Franco. In this article, the authors state that the preparation of the T-1 Raney nickel catalyst is a modification of the procedure described by Papa, Schwenk and Whitman in the Journal of Organic Chemistry 7, 586, (1942) and Papa, Schwenk and Brieger in the Journal of Organic Chemistry, 14, 366, (1949). All of the Raney nickels described in the articles referred to above are operable in the process of this invention.

Other nickel catalysts useful in the invention can be obtained by the use of new techniques known to the catalyst art for depositing metals on suitable supports in a highly dispersed form. These nickel catalysts would exhibit catalytic properties similar to the properties exhibited by the Raney nickel catalysts.

In the article by Dominguez et al, the authors state that the T-1 Raney nickel is prepared as follows:

To a 1-liter 3-neck flask containing 600 ml of a 10 percent sodium hydroxide solution, 40 grams of Raney nickel aluminum alloy (50 percent nickel) were added in small portions over a period of 20 to 30 minutes with mechanical stirring. The temperature was kept at 90°-95° C. during this addition. The mixture was stirred for an additional hour period at which time the stirring was stopped and the nickel was allowed to settle, and the solution decanted. The metal was washed five times with 200-ml portions of water and then five times with 50-ml portions of ethanol in such a manner that the nickel was always covered with liquid. The catalyst was then stored under ethanol and refrigerated for further use.

The Raney nickel employed in some of the examples of this invention, and termed by the present inventor as Modified T-1 Raney nickel, was prepared by a slight modification of Dominguez et al's procedure and is as follows:

A solution of 2 grams of sodium hydroxide in 50-ml of water was heated to its boiling point and then there was added 2 grams of Raney nickel aluminum alloy (1 gram of Raney nickel) as rapidly as the hydrogen evolution would permit. This mixture was then digested at 95° to 100° C. for ¼ hour (reflux) and the water was continually replaced as it evaporated. The solution was decanted from the Raney nickel and the metal washed with three 250-ml portions of cold water. The catalyst was employed without washing with ethanol.

The ratio of catalyst to cyclopentadiene is not too critical. It has been found satisfactory results are obtained when about 1 part by weight of catalyst per 500 parts by weight of cyclopentadiene are employed. It is not advantageous to use a catalyst to cyclopentadiene weight ratio greater than about 1 to 33 is employed since some of the catalyst will be wasted.

The amount of water employed should range from about a volume ratio of water to cyclopentadiene of about 1/1 to about 4/1. More water may be employed, however, the selectivity of the hydrogenation is lowered.

The present invention can be applied to continuous or batch processes. While the ratios of catalyst to cyclopentadiene set forth is applicable to batch processing, those skilled in the art could readily adapt the reactants, catalyst and the reaction conditions to continuous processing.

The practice of this invention is further illustrated by reference to the following examples which are intended to be representative rather than restrictive of the scope of the invention. Unless otherwise indicated, all parts and percentages are by weight.

EXAMPLE 1

A one-liter stainless steel reactor was swept with nitrogen and charged with 150 milliliters (ml) of tap water containing 1.0 gram (g) of modified T-1 Raney nickel suspended by swirling. Thirty-three grams (0.5 mole) of freshly distilled cyclopentadiene containing 1 g of pentane as an internal standard was then added under nitrogen. The sealed reactor was then charged with 150 psig of hydrogen with stirring. The reactor was held at 25° C. with internal cooling coils and the reaction was stopped when 85-90% of the theoretical amount of hydrogen had been consumed, i.e., after about 80 minutes. The reaction was stopped by stopping the stirring and venting the hydrogen pressure to 1 atm. The top organic layer was withdrawn for gas chromatographic analysis. The analysis revealed an 86.2% conversion of cyclopentadiene and a 95.1% selectivity to cyclopentene, with a 3.6% selectivity to cyclopentane.

EXAMPLE 2

A hydrogenation was carried out under the conditions of Example I except that a conversion of cyclopentadiene was increased by employing a 90-minute reaction time instead of 80 minutes. Analysis revealed 93.3% conversion of cyclopentadiene and 86.8% selectivity to cyclopentene with a 14% selectivity to cyclopentane.

EXAMPLE 3

A hydrogenation was carried out under the conditions of Example 2 except that the hydrogen pressure was maintained between 250 and 300 psig. The reaction required only 45 minutes. The analysis revealed 93.6% conversion of cyclopentadiene; 88.4% selectivity of cyclopentene and an 11.5% selectivity to cyclopentane.

EXAMPLE 4

A hydrogenation was carried out under the conditions of Example 3 except that one gram of modified T-1 Raney nickel was suspended in 300 ml of water instead of one gram in 150 ml of water. The reaction required 99 minutes to reach an 85 to 90% consumption of the hydrogen. Analysis revealed 98.0% conversion of cyclopentadiene, 72.0% selectivity to cyclopentene and 24.2% selectivity to cylopentane.

EXAMPLE V

A hydrogenation was carried out under the conditions of Example 4 except that only 100 milliliters of water was employed instead of 300 ml. The reaction required 58 minutes. The analysis revealed 96.4% conversion of cyclopentadiene; 86.2% selectivity to cyclopentene and 11.8% selectivity to cyclopentane.

EXAMPLE VI

A hydrogenation was conducted as in Example 3 except that W-2 Raney nickel was employed instead of the modified T-1 Raney nickel. The reaction required 48 minutes. The analysis revealed 94.6% conversion of cyclopentadiene; 85.3% selectivity to cyclopentene; 14% selectivity to cyclopentane.

While certain representative embodiments and details have been shown for the purpose of illustrating the invention, it will be apparent to those skilled in this art that various changes and modifications may be made therein without departing from the spirit or scope of the invention.

What is claimed is:

1. The process for the preparation of cyclopentene which comprises selectively hydrogenating cyclopentadiene in the liquid phase by contacting cyclopentadiene with hydrogen in the presence of a hydrogenation catalyst comprising a highly dispersed form of nickel selected from the group comprising Raney nickel or modified Raney nickel in which water is employed in the reaction mixture wherein the volume ratio of the water to the cyclopentadiene ranges from 1/1 to 4/1.

2. The process according to claim 1 in which the highly dispersed nickel is Raney nickel.

3. The process according to claim 1 in which the temperature ranges from 20° to 30° C.

4. The process according to claim 1 in which the pressure of the hydrogen is at least 150 psig–1035.5kPa.

5. The process according to claim 1 in which the catalyst is modified T-1 Raney nickel.

* * * * *